(12) United States Patent
Novinski et al.

(10) Patent No.: US 6,861,262 B2
(45) Date of Patent: Mar. 1, 2005

(54) COMPOSITION AND METHOD FOR DETECTING AN ADULTERANT IN AN AQUEOUS SAMPLE

(75) Inventors: John Novinski, Leesburg, FL (US); Barry Sample, Alpharetta, GA (US); Richard L. Hilderbrand, Lady Lake, FL (US); Susan Mills, Ambler, PA (US); Victoria Johnson, Orlando, FL (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 62 days.

(21) Appl. No.: 09/876,716

(22) Filed: Jun. 6, 2001

(65) Prior Publication Data

US 2002/0106807 A1 Aug. 8, 2002

Related U.S. Application Data

(63) Continuation-in-part of application No. 09/517,891, filed on Mar. 3, 2000, now Pat. No. 6,303,384.

(51) Int. Cl.[7] .............................................. G01N 33/00
(52) U.S. Cl. ..................... 436/111; 436/118; 436/140; 436/164; 436/166; 436/172
(58) Field of Search .......................... 436/111, 118, 436/140, 164, 166, 172

(56) References Cited

U.S. PATENT DOCUMENTS

| 3,619,187 A | * | 11/1971 | Cerwonka | ................. 430/288.1 |
| 3,634,198 A | * | 1/1972 | Truhan | ......................... 435/37 |
| 3,719,491 A | * | 3/1973 | Mizianty | .................... 430/150 |
| 3,793,305 A | | 2/1974 | Balon | |
| 3,817,705 A | | 6/1974 | Stein et al. | |
| 3,961,884 A | * | 6/1976 | Hertel et al. | .................. 8/21 C |
| 3,979,262 A | * | 9/1976 | Hunziker | ..................... 435/10 |

(List continued on next page.)

FOREIGN PATENT DOCUMENTS

| DE | 211 873 | | 7/1984 |
| GB | 1282653 | | 3/1970 |
| GB | 1 282 653 | | 7/1972 |
| JP | 63001970 | | 1/1988 |
| SU | 338141 | * | 4/1970 |
| WO | WO 00/52464 | | 9/2000 |

OTHER PUBLICATIONS

Patel "Drug Analysis & Toxicology", MLabs Spectrum, Apr. 1997, vol. 11, No2, Excerpts.*
Raman et al. "Some observatin on the use of p–rosaniline hydrochloride/phloroglucinol for the spectrophotometric deteermination of nitrite", Microchemical Journal (1989), 40 (2), 242–5.*
Butler, "The Diazotization of Heterocyclic Primary Amines", Chem. Rev., 1975, v. 75, pp. 241–257.*
Supplemental European Search Report for related application EP 00916080 mailed Mar. 31, 2003.
International Search Report for corresponding PCT application PCT/US01/18560.
"The Diazotization of Heterocyclic Primary Amines" by Butler; *Chemical Reviews*, 1975, vol. 75, No. 2.

*Primary Examiner*—Yelena G. Gakh
(74) *Attorney, Agent, or Firm*—Stout, Uxa, Buyan & Mullins, LLP; Donald E. Stout; Greg S. Hollrigel

(57) ABSTRACT

It is discovered that a composition comprising at least one amine and at least one stabilizer may be useful in detecting the presence of an adulterant in a urine sample. Such adulterant includes an oxidizing agent.

30 Claims, 7 Drawing Sheets

Response Curve for nitrite solutions treated with DPD / stabilizer reagent

U.S. PATENT DOCUMENTS

| | | | |
|---|---|---|---|
| 4,058,399 A | * 11/1977 | McNeil et al. | 430/259 |
| 4,059,407 A | * 11/1977 | Hochstrasser | 422/56 |
| 4,171,222 A | * 10/1979 | Frommeld | 430/259 |
| 4,434,235 A | 2/1984 | Rabi et al. | |
| 4,631,255 A | * 12/1986 | Takino et al. | 435/37 |
| 4,812,413 A | * 3/1989 | Glattstein et al. | 436/92 |
| 4,978,612 A | 12/1990 | Kobayashi et al. | |
| 5,032,138 A | * 7/1991 | Wolfram et al. | 8/412 |
| 5,413,911 A | 5/1995 | Adamczyk et al. | |
| 5,464,775 A | 11/1995 | Smith | |
| 5,516,700 A | * 5/1996 | Smith et al. | 436/164 |
| 5,527,509 A | 6/1996 | Gibson et al. | |
| 5,703,266 A | * 12/1997 | Lagrange et al. | 558/408 |
| 5,759,860 A | 6/1998 | Smith et al. | |
| 5,801,060 A | 9/1998 | Smith | |
| 5,955,370 A | 9/1999 | Kell | |
| 6,100,394 A | 8/2000 | Collins et al. | |

* cited by examiner

Response Curve for nitrite solutions treated with DPD / stabilizer reagent

Response Curve for Pyridinium Chlorochromate Treated with DPD / stabilizer Reagent Pyridinium Chlorochromate, Absorption vs Concentration $y = -0.0761x^2 + 88.511x + 166.74$
$R^2 = 0.9993$ Response Curve for Sodiumm Hydrochlorite Solutions Treated with DPD / stabilizer Reagent

COMPOSITION AND METHOD FOR DETECTING AN ADULTERANT IN AN AQUEOUS SAMPLE

RELATED APPLICATION

The present application is a continuation-in-part of application Ser. No. 09/517,891, filed Mar. 3, 2000, now U.S. Pat. No. 6,303,384, the disclosure of which is hereby incorporated in its entirety, herein by reference.

BACKGROUND OF THE INVENTION

Drug testing is mandated or strongly supported by many political and regulatory groups and private industry. Hiring or continued employment may depend on a drug-free test. Urine-based testing is a widely practiced way of detecting the use of controlled substances or substances of abuse. Not too surprisingly, those who have found themselves placed in the predicament of having been exposed to certain drugs, either purposefully or inadvertently, and receiving a request for drug testing, have identified and begun using chemicals which mask or interfere with the chemistries used to detect certain drugs. These chemicals are called adulterants. These adulterants can be readily obtained by consumers, being that they have a number of uses and are readily available through many consumer or retail channels. For example, adulterants now showing up with increasing frequency are certain oxidizing agents, particularly nitrite salts, Cr(VI) salts and the alkali metal hypochlorites, e.g., sodium hypochlorite or common bleach.

Various compositions and methods are presently available for detecting an adulterant in urine samples. For example, Kell in U.S. Pat. No. 5,955,370 disclosed a method for detecting a diuretic in a urine sample. However, there continues to be a need for a better composition and method for detecting the presence of adulterants such as oxidizing agents in urine samples.

SUMMARY OF THE INVENTION

This invention provides for that need. In accordance with the present invention, a composition for use in detecting the presence of at least one adulterant in an aqueous sample is featured. The composition comprises at least one amine and at least one stabilizer. An aqueous sample may be a body fluid, for example blood or urine.

Further in accordance with the present invention, an adulterant according to this invention comprises an oxidizing agent. Examples of oxidizing agents include, without limitation, chromates, nitrogen heterocyclic salts of oxidizing agents, peroxides, hypohalites, halite, halates, perhalate, periodide, oxone, permanganate, N-chlorosulfonamides, peracids, oxidative enzymes, nitrites and the like and mixtures thereof.

Still further in accordance with the present invention, the presence of an oxidizing agent is identified by a presence of a range of broad band at about 470 nm to about 604 nm.

Still further in accordance with the present invention, the presence of an oxidizing agent such as a nitrite is identified by a presence of a band at about 408 nm to about 410 nm.

Still further in accordance with the present invention, the amine comprises a primary aromatic amine. For example, the amine comprises N,N-diethylphenylene diamine.

Still further in accordance with the present invention, the stabilizer comprises a creatinine and/or citrate.

Still further in accordance with the present invention, the composition further comprises an iodide. For example, the composition may comprise N,N-diethylphenylene diamine/Iodide/Creatinine/Citrate/Creatinine.

Still further in accordance with the present invention, a method for detecting at least one adulterant is provided. The method comprises the step of combining a composition of the present invention with a urine sample and making a reading of a band which is associated with an adulterant. The step of combining the composition and the urine sample, and the step of reading the absorbance may be achieved manually or by an automated spectrophotometer.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

Figure 1:
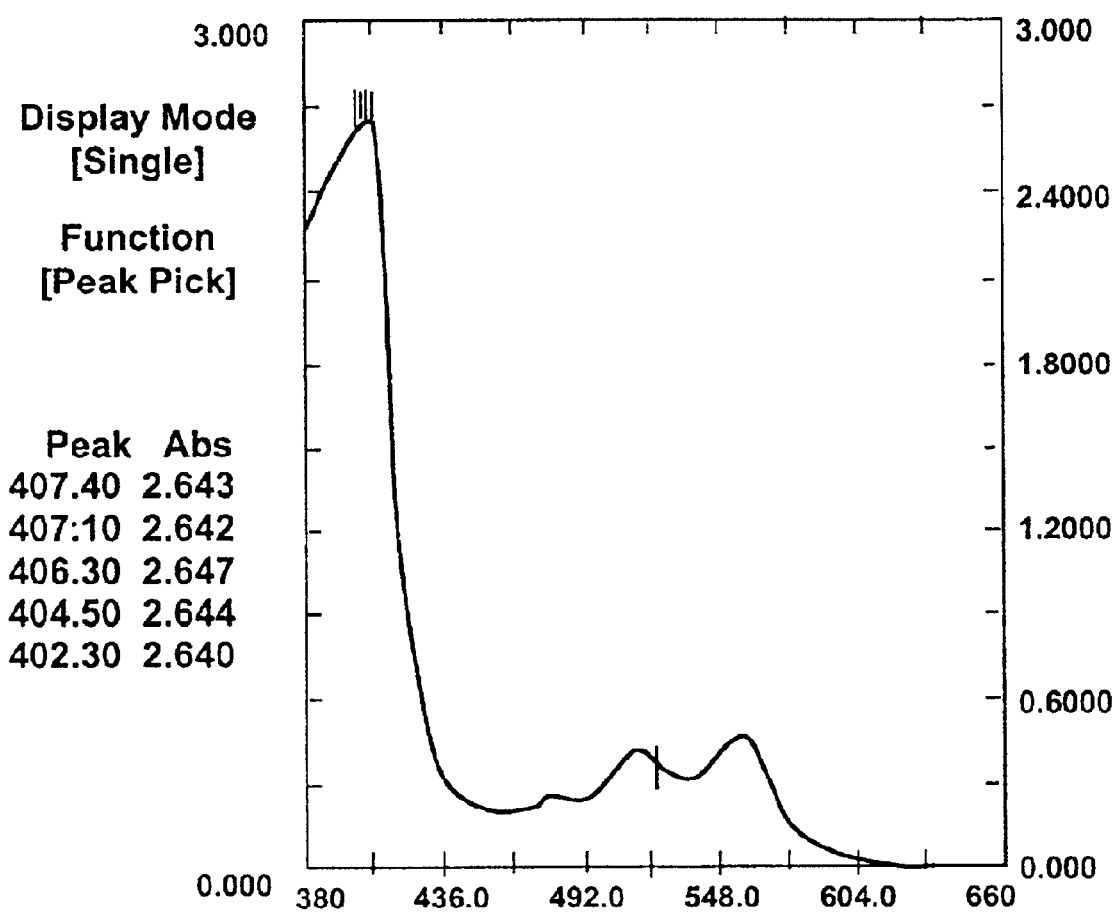
FIG. 1 is a tracing of the visible absorption spectra of a sample treated with DPD and a stabilizing agent to which sodium nitrite has been added.

The present invention is, in part, based upon the discovery that, a composition comprising at least one amine and at least one stabilizer may be useful in detecting the presence of at least one adulterant in an aqueous sample. In one embodiment, an aqueous sample is combined, or added, to a composition to form a mixture, and an adulterant is detected from the mixture. The detection of an adulterant in the mixture is achieved through an observation of absorption band(s) which is/are associated with the respective adulterants. Preferably the observations of the absorption bands are made with a spectrophotometer. As used herein, a band may be a simple band of one peak or a complex band of more than one peak.

An aqueous sample where an adulterant may be detected may include a body fluid. In one embodiment, a body fluid includes a blood sample, a tear sample and/or, preferably, a urine sample.

As used herein, an adulterant is any chemical, composition or complex which may interfere with the detection of a test compound. These adulterants may be added to the aqueous sample to be tested. For example, a person may add an adulterant to his or her urine sample to prevent the detection of the presence of a test compound. A test compound includes a drug precursor, a drug, a drug metabolite and/or any molecule suggesting that there is a presence of a drug in the test urine. Non-limiting examples of a drug includes opioids (e.g. Heroin, morphine, methadone, codeine), CNS depressants (e.g. barbiturates, phenobarbital, benzodiazephines valium, Librium), psychostimulants (e.g. cocaine, amphetamines, methamphetamines, "crack"), cannabinoids (e.g. marihuana, hashish, tetrahydrocannabinol, cannabinol, cannabidiol), psychedelics (e.g. hallucinogens, psychotomimetics, psychotogens, lysergic acid diethylamide, mescaline, peyote, psilocybin, "magic" mushrooms), arylcyclohexylamines (e.g. phencyclidine, "angel dust", "crystal", PCP).

In one embodiment, an adulterant comprises any molecule or complex which is capable of preventing the detection of another chemical entity. In a preferred embodiment, an adulterant comprises an oxidizing agent. An oxidizing agent as used herein may be any material which is capable of directly or indirectly facilitating the oxidation of another chemical entity, preferably a chemical molecule, more preferably a test compound, even more preferably a drug or a drug metabolite. Preferably, the oxidizing agent prevents the detection of a presence of a drug in an aqueous sample, for example a urine sample.

One type of oxidizing agent comprises a transition metal. Preferably, the transition metal has a high oxidation state. An example of such an oxidizing agent includes a chelate complex. See, for example, Collins et al. U.S. Pat. No. 6,100,394, the disclosure of which is incorporated in its entirety herein by reference. Another example of such oxidizing agent includes a transitional metal salt. In one embodiment, an oxidizing agent comprises chromium compounds. Preferably, these oxidizing agents comprise Chromium (VI) compounds, for example, chromate salts, pyridinium chlorochromate, pyridinium fluorochromate, chromium oxide, dichromate and the like and mixtures thereof. In another preferred embodiment, an oxidizing agent comprises vanadium compounds, for example sodium meta vandate (V). In yet another preferred embodiment, these oxidizing agents comprise Cerium (IV) compounds, for example ammonium hexanitrato cerate (IV).

Another type of oxidizing agent comprises a nitrite, alkyl nitrite, arylnitrite, nitrous acid, the like and mixtures thereof. Yet another type of oxidizing agents comprises nitrogen heterocyclic salts of oxidizing agents, for example, pyridinium hydrogen perbromide, quinolinium dichromate, the like and mixtures thereof.

Other types of oxidizing agents include peroxides (e.g. hydrogen peroxide), hypohalites (e.g., hypochlorite, hypobromite), ferricyanide, halites (e.g., chlorite), halates (e.g., chlorate), perhalate (e.g., perchlorate), periodide, oxone, permanganate, N-chlorosulfonamides (e.g., chloroamine-T, chloroamine-B), peracids (e.g., perselenic acid, 3-chloroperbenzoic acid), oxidative enzymes (e.g., catalase, peroxidase, microperoxidase), the like and mixtures thereof.

In one embodiment, the oxidizing agent as used herein does not include a nitrite, alkyl nitrite, arylnitrite, nitrous acid, the like and mixtures thereof.

In one embodiment, the composition comprises a nitrogen containing molecule, for example an azine or a diphenylazine. Preferably, the composition comprises an amine. In a preferred embodiment, the amine comprises an aromatic amine. More preferably, the amine comprises a primary aromatic amine, for example a primary aromatic diamine. The aromatic group of the primary aromatic amine may have about 4 to about 10 carbons, preferably 6 carbons. Additionally, the aromatic group of the primary aromatic amine may be a heterocyclic molecule.

Chart 1 shows non-limiting examples of amines that may be used in accordance with the present invention.

Chart I

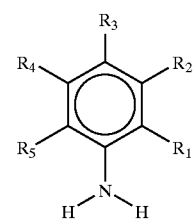

Compound I

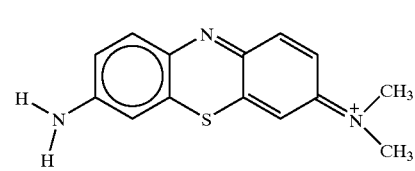

Compound II

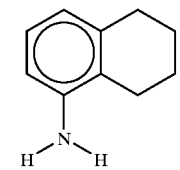

Compound III

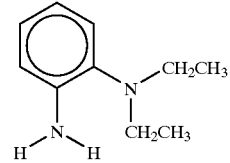

Compound IV

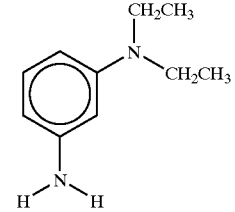

Compound V

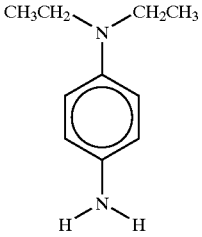

Compound VI

With respect to compound I, $R_1$, $R_2$, $R_3$, $R_4$, and $R_5$ may each individually be an alkyl (e.g., methyl, ethyl, isopropyl, t-butyl and n-butyl), aryl, a hydrogen, a halogen, hydrocarboxy, carboxylic acid ester, sulfonic acid ester or amino. In a preferred embodiment, the alkyl comprises about 2 to about 10 carbons, more preferably about 2 to about 5 carbons. The amino may be $R_6$—N—$R_7$, where $R_6$ and $R_7$ may each individually be an alkyl, aryl group, hydrogen, halogen, hydrocarboxy, carboxylic acid ester or sulfonic acid ester.

Furthermore, $R_1$, $R_2$, $R_3$, $R_4$, and $R_5$, or $R_6$ and $R_7$ may bridge with each other. Compound II is an example of a bridging between $R_2$ and $R_3$. Compound III is an example of a bridging between $R_1$ and $R_2$.

In a preferred embodiment, the amine is an o, m or p-N,N-diethylphenylene diamine (hereinafter "DPD"), compounds IV, V and VI, respectively (Available from Aldrich catalog no. 26151-3). In a more preferred embodiment, the amine is a p-DPD (compound VI).

Other amines, or preferably primary aromatic amines, may include anilines (e.g., para-ethoxyaniline, ethylaniline, diethylaniline, toluidines, xylidenes), 2-methyl-4-amino-5-formylamino pyridimidine, 2-methyl-4-amino-5-pyrimidinecarboxylic acid, 1,5 dimethyl-6-aminonaphthaline, the like and mixtures thereof. In one embodiment, the amine may be a secondary aromatic amine, for example anilinopyridine.

In one embodiment, an amine in accordance with the present invention may be a $NH_2$ covalently linked to a conjugated system, forming a conjugated-system-amine. The conjugated-system may be a carbon-chain. A carbon conjugated system may comprise 3 to 15 carbons, preferably 4 to 8 carbons. For example, an amine in accordance with the present invention may be $NH_2CH=CH—CH=CH_2$. The conjugated system may also include a heteroatom. For example, an amine in accordance with the present invention may be $NH_2C=N—N=C$.

The amount of amine, for example aromatic amine, preferably primary aromatic amine, used will be some concentration sufficient to give a useful visible absorption spectra. Generally, the amine is at a concentration of about 0.1 g/L to about 1.2 g/L, preferably about 0.3 g/L to about 0.9 g/L, more preferably about 0.6 to about 0.8 g/L of the composition. At the time an absorption reading is made, it is preferable that the concentration of the composition be diluted, for example with water. In one embodiment, the composition is diluted to about half the original concentration, at the time an absorption reading is made. The dilution is especially advantageous when the aqueous sample is suspected of containing a transition metal oxidizing agent. Furthermore, it is preferable that the amine is dissolved in a suitable solvent prior to being added to the test sample. Various solvents can be used so long as the compound dissolves in it. In one embodiment, organic type or aprotic solvents are used. For example, when DPD is used, it is convenient to first dissolve it in a short-chain organic acid such as formic acid, glacial acidic or acetic acid before diluting it further with water.

Figure 7:
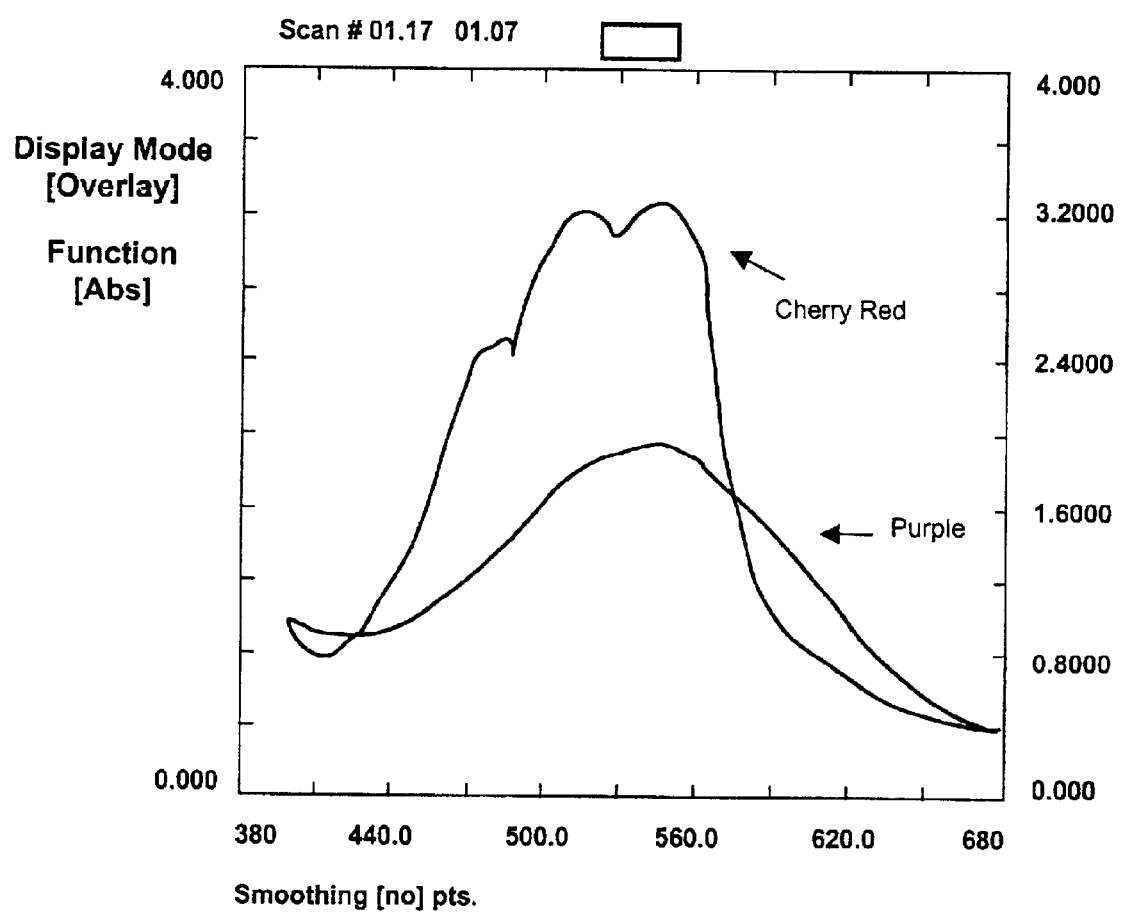
FIG. 7 is a tracing of a visible absorption spectra showing a "cherry red" band and a "purple" band.

In one embodiment, the composition comprises a stabilizer. Without wishing to limit the invention to any particular mechanism or theory of operation, it is believed that the stabilizer stabilizes a species which gives rise to a band associated with at least one adulterant. In some situations, it is further believed that the stabilized species is an adulterant-stabilizer intermediate, for example an (oxidizing agent)-DPD intermediate. In any case, the stabilized species gives rise to a more persistent band. For example, the stabilizer may facilitate an increase in the life-time of a band associated with the oxidizing agent. In one embodiment, the stabilizer increases the lifetime of a band associated with the oxidizing agent, wherein the band is not defined by the purple spectra region, see FIG. 7.

In a preferred embodiment, the stabilizer helps maintain a band associated with an adulterant for a period of time long enough for adequate measurement of a band. In a more referred embodiment, the stabilizer helps maintain a band associated with an adulterant for at least about 30 seconds. A stabilizer useful in this invention includes any molecule or chemical entity having at least one non-bonding pair of electrons. For example, a stabilizer may be any nucleophile. Preferably, a stabilizer is an oxygen or nitrogen containing molecule. Non-limiting examples of stabilizers include sodium ethoxide, sodium hydroxide, creatinine, citrate salt and mixtures thereof. In a preferred embodiment, a stabilizer is a creatinine (available from Sigma Catalog No. C4255). In another preferred embodiment, a stabilizer is a citrate. In yet another embodiment, the composition of the present invention comprises at least two stabilizers, for example a creatinine and a citrate.

In one embodiment, a stabilizer according to the present invention is not used as an acid.

An effective concentration of the stabilizer in the composition is about 1 g and 6 g, preferably about 2 g and about 5 g, more preferably about 4 g to about 4.5 g/L. At the time an absorption reading is made, it is preferable that the concentration of the stabilizer in the composition be diluted, for example with water. In one embodiment, the original concentration of the stabilizer in the composition is diluted to about half at the time an absorption reading is made.

The composition is effective in aiding in the detection of at least one adulterant in an aqueous sample when it is added or combined with the aqueous sample. In one embodiment, a small volume of an aqueous sample may be added to a composition of the present invention to form a mixture. For example, about 1 to about 5 uL of an aqueous sample may be added to about 100 to about 300 uL of the composition, or similar ratios. In a preferred embodiment, about 3 uL of an aqueous sample may be added to 250 uL of the composition, or similar ratios. Preferably, the aqueous samples above are urine samples.

A mixture containing an adulterant, for example an oxidizing agent, will have an absorption band or set of bands characteristic of that type of adulterants. These particular bands may be determined empirically through commonly known methods by one of ordinary skill in the art.

In one embodiment, the various types of oxidizing agents identified above may be generally categorized into two classes. The first class of oxidizing agents, class I, may be identified by an absorption of a broad complex band at about 470 nm to about 604 nm, or as is substantially described in FIGS. 2 and 3. Examples of the class I oxidizing agents include, without limitation, the chromium compounds and hypochlorites. The second class of oxidizing agents, class II, may be identified by a strong absorption band at about 408 nm to about 420 nm, preferably at about 410 nm, and a weak absorption band at about 470 nm to about 620 nm, preferably at 511 nm. FIG. 1 substantially describes the absorption characteristics of class II oxidizing agents. A non-limiting example of a class II oxidizing agent includes a nitrite.

The absorption band at about 470 nm to about 604 nm may sometimes be referred to herein as the "cherry red" band. In most cases, this band is relatively short-lived and is usually not amenable for detection and measurement. For example, in urine samples, this band exists for less than a second. As such, the detection of certain class II oxidizing agents, for example chromium compounds, in urine would be difficult or nearly impossible. However, it has been surprisingly discovered that the unique elements of the present composition allow for this cherry red band to be persistent enough to be detected and measured. Preferably, the composition of the present invention enhances the lifetime of the cherry red band in a urine sample. The exact chemical basis behind this phenomenal is presently unknown. Without wishing to limit this invention to any mechanism or theory of operation, it is believed that the cherry red band reflects an intermediate which is formed when an oxidizing agent is placed in the present composition.

In one embodiment, the cherry red band persists for at least about 15 seconds to about 10 minutes, preferably 5 minutes. In a preferred embodiment, the cherry red band persists for at least about 30 seconds to about 3 minutes. In a more preferred embodiment, the cherry red band persists for at least about 40 seconds to about 2 minutes. In one embodiment, the composition further comprises an iodide. Without wishing to limit the invention to any mechanism or theory of operation, it is believed that the inclusion of an iodide in the composition increases the lifetime of the cherry red band. This increased time allows for a better detection and measurement of the band. Preferably, the molar ratio of the iodide to the amine is about two to about ten, preferably about three to about seven, more preferably about five. For example, a preferred composition comprises iodide in about five molar excess of DPD. In one embodiment, the composition comprises about 2 g to about 8 g, preferably 4.5 g of iodide salt, for example sodium iodide, per 1000 mL. At the time an absorption reading is made, it is preferable that the concentration of the iodide be diluted, for example with water. In one embodiment, the iodide concentration is diluted to about half at the time an absorption reading is made.

In one embodiment, the composition is effective in facilitating the detection of a single adulterant, preferably an oxidizing agent. For example, the composition may facilitate in the detection of class II oxidizing agents (such as a nitrite), which is characterized by a strong absorption band at about 408 nm to about 420 nm, preferably about 410 nm, and a weak absorption band at about 470 nm to about 604 nm, preferably 570 nm; or the composition may facilitate in the detection of class I oxidizing agents (such as a hypochlorite), which is primarily characterized by the absorption band at about 408 nm to about 604 nm, preferably 570 nm.

In a preferred embodiment, the composition is effective in facilitating the detection of more than one adulterant, preferably more than one oxidizing agent. For example, a composition of the present invention may be useful in facilitating a simultaneous detection of both class I and class II oxidizing agents. See Example 5 below.

Furthermore, the composition of the present invention may be useful in facilitating the detection of one or more types of oxidizing agents within the same class. For example, the cherry red complex band may reflect a detection of a single oxidizing agent, for example hypochlorite, but the cherry red complex band may also reflect a measurement of more than one type of oxidizing agents belonging to the same class, such as a hypochlorite and a pyridinium chlorochromate. In the latter case, the cherry red complex band may reflect a summation of an absorption from a species indicative of a hypochlorite and an absorption from a species indicative of chlorochromate.

In one embodiment, the detection of an oxidizing agent is not by the detection of a band associated with the purple region of the visible spectrum. That is, in one embodiment, the oxidizing agent is not detected by an observation of a band having wavelengths of about 670 nm.

Compositions of the present invention may be appropriate for use in a spot test. For example, a person may add an effective quantity of the present composition to a test tube containing a suspect urine sample. The person may then observe for a transitional cherry red color from the composition/urine mixture with the naked eye. An identification of a transitional cherry red color in the test tube is indicative that the urine may be adulterated with at least one oxidizing agent, for example a chromium compound.

Preferably, the detection of an adulterant using the present compositions is facilitated by a spectrophotometer. For example, instead of observing for the transitional presence of the cherry red color with a naked eye, it is preferred that the composition/urine mixture be placed in a spectrophotometer for a detection of a band at about 470 nm to about 604 nm. The detection of such a band is indicative that the urine may contain an adulterant, for example a hypochlorite. Additionally, the spectrophotometer may detect for absorptions at other wavelengths, for example at about 408 nm to about 420 nm, preferably 410 nm. A detection of a strong an absorbance at about 408 nm to about 420 nm, and a weak absorbance at about 470 nm to about 604 nm suggests that the urine may be adulterated with another type of oxidizing agents, for example nitrites.

More preferably, the detection of an adulterant using the present composition is facilitated by an automated spectrophotometer. In some situations, certain transitional bands appear within seconds after the composition is mixed with the suspect urine. For example, a detection of the absorption bands associated with DPD stabilized products must be made within seconds after the mixing of the composition and the urine. Any automated spectrophotometer may be employed for the purpose of this invention, provided that it is capable of making a reading relatively quickly (e.g., less than a few minutes, preferably less than a few seconds) after the composition and the aqueous sample is mixed. Non-limiting examples of automated spectrophotometers include the Olympus AU-800, AU-5000, AU-5200, AU-5400, Hatatchi 717, Hatatchi 747 and Beckman DU70 can be programmed to make absorption measurements within less than 30 seconds of mixing the composition and the aqueous sample.

In one embodiment, the observation of bands associated with certain adulterants may be qualitative. However, the absorption bands may yield quantitative data by preparing a calibration curve within the specified wavelengths. The calibration curve may be prepared by methods commonly known in the art.

In one embodiment, the composition comprises an N,N-diethylphenylene diamine and a creatinine. This composition may be employed in accordance with this invention to detect the presence of one or more types of oxidizing agents, for example a hypochlorite, a pyridinium chlorochromate, and a hydrogen peroxide. Preferably, the composition may additionally be employed in accordance with this invention to detect one or more class of oxidizing agents, for example class I comprising chromium compounds and class II comprising nitrites. Even more preferably, the composition may be employed to detect the presence of more than one class of oxidizing agents simultaneously. The concentration of the N,N-diethylphenylene diamine and a creatinine in this composition may be about 0.4 g/L and 2 g/L of the final composition/aqueous sample mixture volume, respectively. Preferably, the composition is employed to detect for these adulterants in a urine sample. In one embodiment, prior to adding the aqueous sample to the composition and prior to absorption reading, the concentrations of the amine and stabilizer in the composition may be twice the final composition/aqueous sample mixture concentrations. A dilution of the composition may be achieved with adding water immediately prior to adding the aqueous sample, for example urine sample, or immediately prior to absorption reading.

In one embodiment, the composition comprises (a) more than one amine, for example an N,N-diethylphenylene diamine and an aniline, and (b) one or more stabilizer, for example citrate and/or creatinine. This composition may be employed in accordance with this invention to detect adulterants, such as oxidizing agents. The concentration of the N,N-diethylphenylene diamine and aniline here may be about 0.2 g to about 0.4 g and about 0.1 g to about 0.4 g per the composition/urine sample mixture, respectively. If only one stabilizer is used, the citrate or creatinine concentrations may be about 2 g or about 2.5 g per the final volume of the composition/urine sample mixture, respectively. If a combination of stabilizer is used, the citrate and creatinine concentration may be 2.25 g and 1.15 g per the final volume of the composition/urine sample mixture, respectively. Preferably, the composition is employed to detect for these adulterants in a urine sample. In one embodiment, prior to adding the aqueous sample to the composition and prior to absorption reading, the concentrations of the amine and stabilizer(s) in the composition may be twice the final composition/aqueous sample mixture concentrations. A dilution of the composition may be achieved with adding water immediately prior to adding the aqueous sample, for example urine sample, or immediately prior to absorption reading.

In a preferred embodiment, the composition comprises an N,N-diethylphenylene diamine, iodide, citrate and creatinine. This composition may be employed in accordance with this invention to detect the presence of one or more class of oxidizing agents, for example a hypochlorite, a pyridinium chlorochromate, and a hydrogen peroxide. Preferably, the composition may additionally be employed in accordance with this invention to detect one or more groups of oxidizing agents, for example the group comprising chromium compounds and the group comprising nitrites. Even more preferably, the composition may be employed to detect the presence of more than one group of oxidizing agents simultaneously. The concentration of the N,N-diethylphenylene diamine, iodide, citrate and a creatinine in this composition may be about 0.1–0.5 g, about 1.0–3.5 g, about 1.0–2.0 g and about 1.5–3.0 g per the 1 liter vol of the final composition/urine sample mixture, respectively. Preferably, the concentration of the N,N-diethylphenylene diamine, iodide, citrate and a creatinine in this composition may be about 0.3 g, about 2.25 g, about 1.25 g and about 2.25 g per the 1 liter volume of the final composition/urine sample mixture, respectively. In one embodiment, prior to adding the aqueous sample to the composition and prior to absorption reading, the concentrations of the N,N-diethylphenylene diamine, iodide, citrate and a creatinine in the composition may be twice the final composition/aqueous sample mixture concentrations. A dilution of the composition may be achieved with adding water immediately prior to adding the urine sample, or immediately prior to absorption reading.

In one embodiment, the composition has a pH of about 5 to about 8, preferably about 6 to about 7.5, more preferably about 6.5 to about 7.5. Without wishing to limit the invention to any particular theory or mechanism of operation, it is believed that the present invention may function more properly at a neutral pH, not an acidic pH. In a preferred embodiment, the composition/aqueous sample has a neutral pH at the time an absorption reading is made.

In one embodiment, a composition of the present invention may be used to detect oxidizing agents other than nitrite and the like.

Although a composition according to the present invention is preferably a solution, the composition may be also a gel or a solid. In one embodiment, a solid composition may be formed by dissolving DPD in a polymer that has the characteristics of a stabilizer. Such stabilizer may comprise nucleophilic groups attached to a polymer backbone, for example polyvinylalcohol. In another embodiment, a solid composition may be formed by dissolving DPD in a polymer such as gelatin. The DPD/gelatin may then be sandwiched between two layers of gelatin in which the stabilizer has been dissolved. Preferably, the layers are thin, for example a micron or less in thickness. In yet another embodiment, both the DPD and the stabilizer may be dissolved in a polymer. Preferably, such polymer allows for the DPD and the stabilizer to substantially interact as though they are in solution.

The following examples are provided to illustrate the invention but are not intended to limit it in any fashion or to any degree.

EXAMPLE 1

DPD/Creatinine Composition

A composition for detecting the presence of oxidizing agents such as nitrites, chlorochromates and/or hypochlorites is prepared as follows:

Creatinine (about 3 g to about 5 g, preferably 4 g) is dissolved in about 1000 mL of deionized water. Then dissolve about 0.5 g to about 1 g, preferably about 0.8 g of N,N diethyl-1,4-phenylene diamine in 60 mL of glacial acetic acid. To this latter solution, add enough of the creatinine solution prepared above to give a volume of 1000 mL. This creatinine/diamine solution is then ready for use in a colorometric assay for detecting a nitrite and/or an oxidizing agent. Preferably this composition is used in conjunction with a urine sample. In one embodiment, the composition has a neutral pH.

EXAMPLE 2

Method of Detecting an Adulterant in Urine

Obtain urine sample from a patient. In one embodiment, the urine does not contain an additive and is maintained at room temperature, for example about 25° C. to about 30° C., preferably about 27° C. Furthermore, it is preferable that the urine be analyzed within about 20 hours, more preferably within about 10 hours, even more preferably within about 6 hours after it is extracted from a person or animal.

Prepare a composition according to Example 1. Place about 250 uL of the composition into a cuvette. Preferably the composition is maintained at 25–30° C., more preferably 27° C., at all times. Add to the cuvette containing the composition about 250 uL of deionized water and about 3 uL of a test urine. Immediately after the addition of water and urine, determine the presence of a band at about 408 nm to about 420 nm, preferably 410 nm, and a complex band at about 470 nm to about 604 nm, preferably 540 nm. A presence of a former band is indicative of a nitrite adulterant in the urine; a presence of a latter complex band is indicative of an oxidizing agent in the urine.

The step of adding the composition, water and urine sample to the cuvette, and the step of determining the presence of certain bands may be conducted manually. Preferably, these steps may be achieved by an automated spectrophotometer, provided that the automated machine is able to make a reading of the absorbance in about less than 40 seconds after the urine is added to the composition. Readings of the absorbance are made at about 25° C. to about 30° C., preferably about 27° C.

EXAMPLE 3

DPD/Iodide/Creatinine/Citrate/Creatinine Composition

A composition for detecting the presence of oxidizing agents such as nitrites, chlorochromates and/or hypochlorites is prepared as follows:

Dissolve Iodide (about 3 g to about 6 g, preferably about 4.5 g), creatinine (about 3 g to about 6 g, preferably about 4.5 g) and citrate (about 1 g to about 4 g, preferably about 2.5 g) in about 1000 mL deionized water. Then dissolve about 0.6 g of N,N diethyl-1,4-phenylene diamine in about 80 mL of glacial acetic acid. To this latter solution, add enough of the iodide/creatinine/citrate solution prepared above to the give a volume of 1000 mL. The iodide/creatinine/citrate/diamine solution is then ready for use in a colorometric assay for detecting a nitrite and/or an oxidizing agent. Preferably, this composition is used in conjunction with a urine sample. In one embodiment, the composition has a neutral pH.

EXAMPLE 4

Method of Detecting an Adulterant in Urine

Prepare a composition according to Example 3. Place about 250 uL of the composition into a cuvette. Add to the cuvette containing the composition about 250 uL of water and 3 uL of a test urine. Immediately after the addition of the water and urine, determine the presence of a band at about 408 nm to about 420 nm, preferably 410 nm, and a complex band at about 470 nm to about 604 nm, preferably 540 nm. A presence of a former band is indicative of a nitrite adulterant or the like in the urine; a presence of a latter complex band is indicative of an oxidizing agent, for example hypochlorite and/or pyridinium chlorochromate, in the urine.

The step of adding the composition, water and urine sample to the cuvette, and the step of determining the presence of certain bands may be conducted manually. Preferably, these steps may be achieved by an automated spectrophotometer, provided that the automated machine is able to make a reading of the absorbance in about less than 40 seconds after the urine is added to the composition. Readings of the absorbance are made at about 25° C. to about 30° C., preferably about 27° C.

EXAMPLE 5

Distinguishing between a Nitrite and other Oxidizing Agents in a Single Assay

A mixture containing a nitrite shows a sharp absorption band at about 408 nm to about 420 nm, and a small complex band at about 470 nm to about 604 nm. A mixture containing the other group of oxidizing agents, for example hypochlorite, also shows an absorption of a complex band at about 470 nm to about 604 nm.

Thus, to determine the presence of non-nitrite oxidizing agents, subtract the absorption in the range of the broad band (470 nm to 604 nm) for the non-nitrite oxidizing agent from the absorption in the sharp absorption (408 nm to 420 nm) of the nitrite. (The absorption is quantified either by the area of the band or the height of the band.) A positive number may be indicative of the presence of nitrite and a negative number may be indicative of the presence of a halogen containing bleach. In one embodiment, a positive number may be indicative that there is a higher concentration of nitrite than non-nitrite oxidizing agent; and a negative number may be indicative that there is a higher concentration of oxidizing agent than nitrite.

In one embodiment, the instrument used may detect only one band. In another embodiment, the instrument used may simultaneously detect more than one band, for example two bands. The use of a particular instrument is readily known to one of ordinary skill in the art.

EXAMPLE 6

Figure 2:
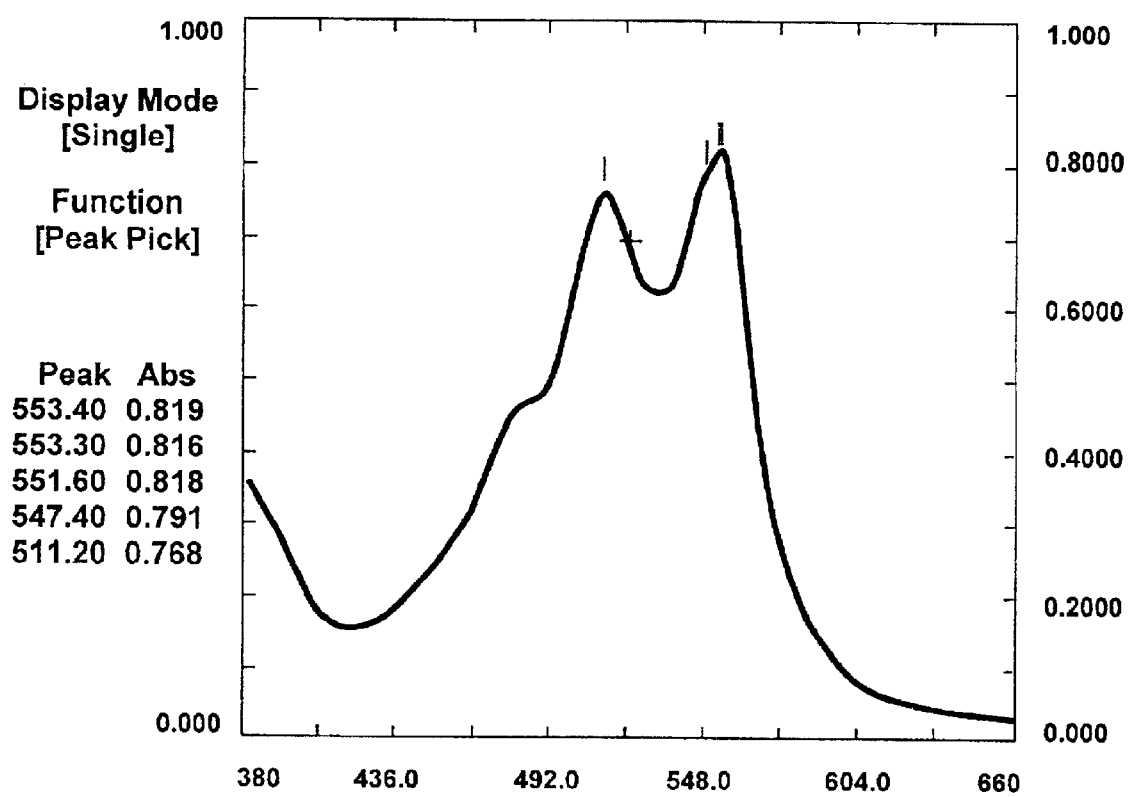
FIG. 2 is a tracing of the visible absorption spectra from a sample containing DPD and a stabilizing agent to which sodium hypochlorite has been added.
Figure 3:
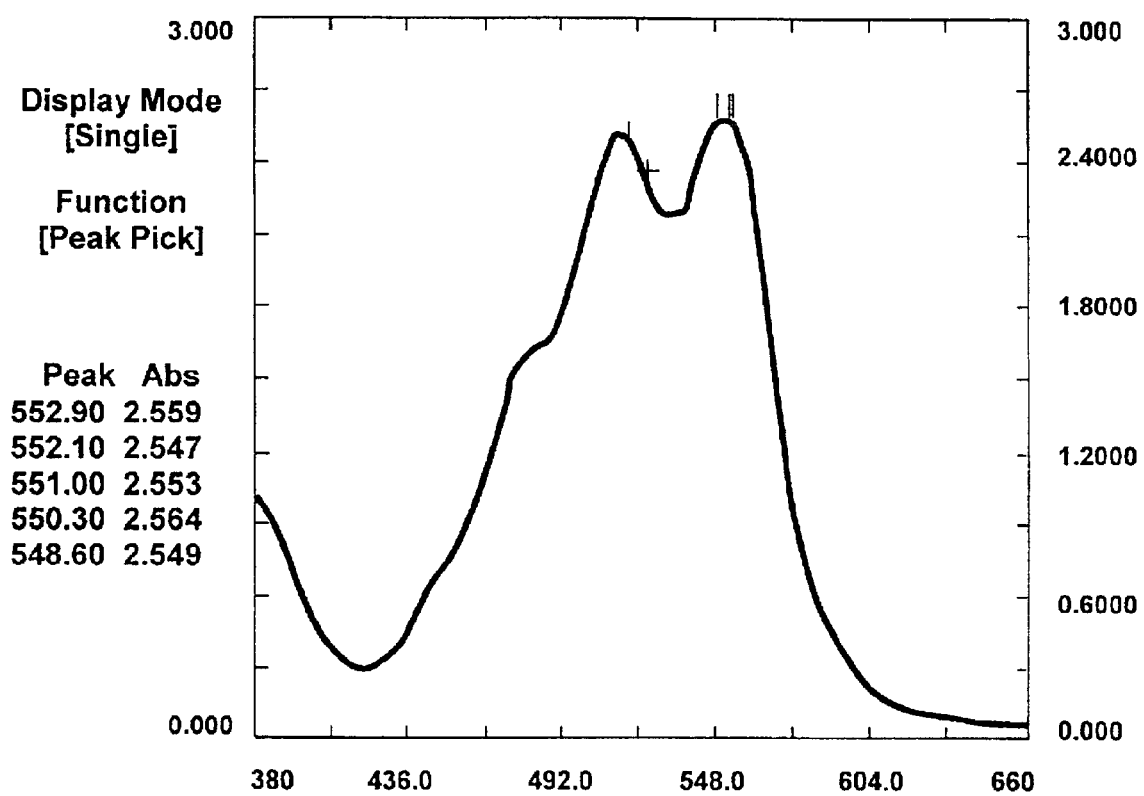
FIG. 3 is a tracing of a visible absorption spectra from a sample containing DPD and a stabilizing agent to which pyridinium chlorochromate has been added.

FIGS. 1 and 2 set out the visible spectra for the DPD composition prepared in Example 1 when sodium nitrite, sodium hypochlorite and pyridinium chlorochromate are added. The visible spectra associated with the sodium hypochlorite are identical to the visible spectra associated with the pyridinium chlorochromate. It can easily be seen that the sodium nitrite produces an intense absorption at about 411 nm and a weak absorption at around 540 nm. Sodium hypochlorite generates an intense absorption only at 540 nm as does pyridinium chlorochromate. The method is useful for concentrations of sodium nitrite up to two thousand ug/ml. A high concentration of sodium hypochlorite (20% solutions) increases the lifetime of the cherry-red band. Results are shown in Table 1. These results are based on readings taken with the spectrophotometer set to record at 410 nm and 540 nm.

TABLE 1

Absorbances for NaNo$_2$, NaOCl, and Pyridinium Chlorochromate

| NaNo$_2$ Conc. | Absorption | Pyridinium Chloromate | Absorb. | NaOCl | Absorb. |
|---|---|---|---|---|---|
| 200 µg/ml | 1647 | 125 ppm | −79.25 | 0.05% | −742.2 |
| 400 µg/ml | 3230 | 250 ppm | −159.6 | 0.21% | −1724.8 |
| 500 µg/ml | 4158 | 500 ppm | −320.2 | 0.32% | −2212.4 |
| 1000 µg/ml | 9280 | 1000 ppm | −601.4 | 0.52% | Flagged as high |
| 2000 µg/ml | | | | 1.58% | Flagged as high |

TABLE 2

Spectrophotometer Parameters-Olympus AU800

| Description | Setting |
|---|---|
| Sample vol.: | 3 uL |
| Composition vol. | 250 uL |
| Diluent vol.: | 250 uL |
| Wavelength 1: | 410 nm |
| Wavelength 2: | 540 nm |
| Method | End |
| Reaction slope | + |
| Measure Pt | $S_1 = 0$ |
| | $E_1 = 1$ |

EXAMPLE 7

Validation Studies

Validation studies were performed to evaluate the following parameters for nitrite, pyridinium chlorochromate and sodium hypochlorite:

Linearity—The linear range at multiple concentration ranges above and below the cutoff were evaluated.

Precision—Intra-run precision was evaluated at the concentration ranges used for linearity evaluation. Inter-run precision was evaluated on quality control samples spiked at +25% and −25% of cutoff.

Nitrite: Specimens were tested for nitrite using a current nitrite reagent and DPD and creatinine as prepared in Example 1.

Pyridinium Chlorochromate: Specimens tested for pyridinium chlorochromate and found to be positive were also evaluated by gas chromatography/mass spectrometry to confirm the presence of the adulterant.

Sodium hypochlorite (bleach): Specimens were tested for bleach and found to be positive were also evaluated using an AquaCheck dipstick to confirm the presence of chlorine.

Carryover—High concentrations of nitrite, pyridinium chlorochromate and bleach were evaluated along with negative controls to determine the level at which carryover occurs in the testing process.

Olympus AU 5061 and AU800 chemistry analyzers were used for recording absorbance spectra.

In each of these assays the target adulterant was spiked into deionized water for nitrite and urine for pyridinium chlorochromate and bleach and then DPD/creatinine composition prepared as per Example 1 was added as described below.

EXAMPLE 7(a)

Sodium Nitrite Evaluation with DPD/Creatinine Composition

Table 3 sets outs results observed when solutions containing increasing concentrations of sodium nitrite were treated with DPD/creatinine composition described in Example 1. Water was spiked with sodium nitrite to give different concentrations of nitrite as the starting point for generating an absorbance curve. Spiked samples were processed through an Olympus AU800 autoanalyzer which sampled a 3 µl aliquot of the spiked specimen, mixed it with 250 ml of the DPD/creatinine composition described in Example 1 and 250 ml of deionized water. The analyzer control software was set to S1=0 and E1=2 and a reading was taken at 410 nm. These settings allow for an absorption reading at about 30 seconds after the composition is mixed with the urine.

Readings up to 200 µg/ml are considered to reflect unadulterated samples. Samples with readings between 201 and 499 µg/ml are flagged as being unacceptable and samples with readings of 500 µg/ml or higher are retested for nitrites using a second colorometric assay.

TABLE 3

Nitrite Evaluation with DPD/Creatinine Composition

| Nitrite Conc. µg/ml | Assayed Values (concentration units) | | | | | Average |
|---|---|---|---|---|---|---|
| 50 | 54 | 56 | 56 | 55 | 50 | 54 |
| 100 | 106 | 112 | 108 | 108 | 106 | 108 |
| 250 | 246 | 267 | 260 | 263 | 256 | 258 |
| 375 | 373 | 398 | 383 | 379 | 372 | 381 |
| 500 | 479 | 504 | 501 | 491 | 487 | 492 |
| 625 | 597 | 645 | 619 | 629 | 611 | 620 |
| 750 | 690 | 737 | 729 | 733 | 700 | 718 |
| 1000 | 885 | 961 | 930 | 905 | 905 | 917 |
| 2000 | 1498 | 1553 | 1561 | 1580 | 1475 | 1533 |

TABLE 3-continued

Nitrite Evaluation with DPD/Creatinine Composition

| Nitrite Conc. µg/ml | Assayed Values (concentration units) | | | | | Average |
|---|---|---|---|---|---|---|
| 3000 | 1887 | 1997 | 1928 | 1931 | 1881 | 1925 |
| | Series 1 | Series 2 | Series 3 | Series 4 | Series 5 | Series 6 |

EXAMPLE 7(b)

Pyridium Chlorochromate Evaluation with DPD/Creatinine Composition

Figure 4:
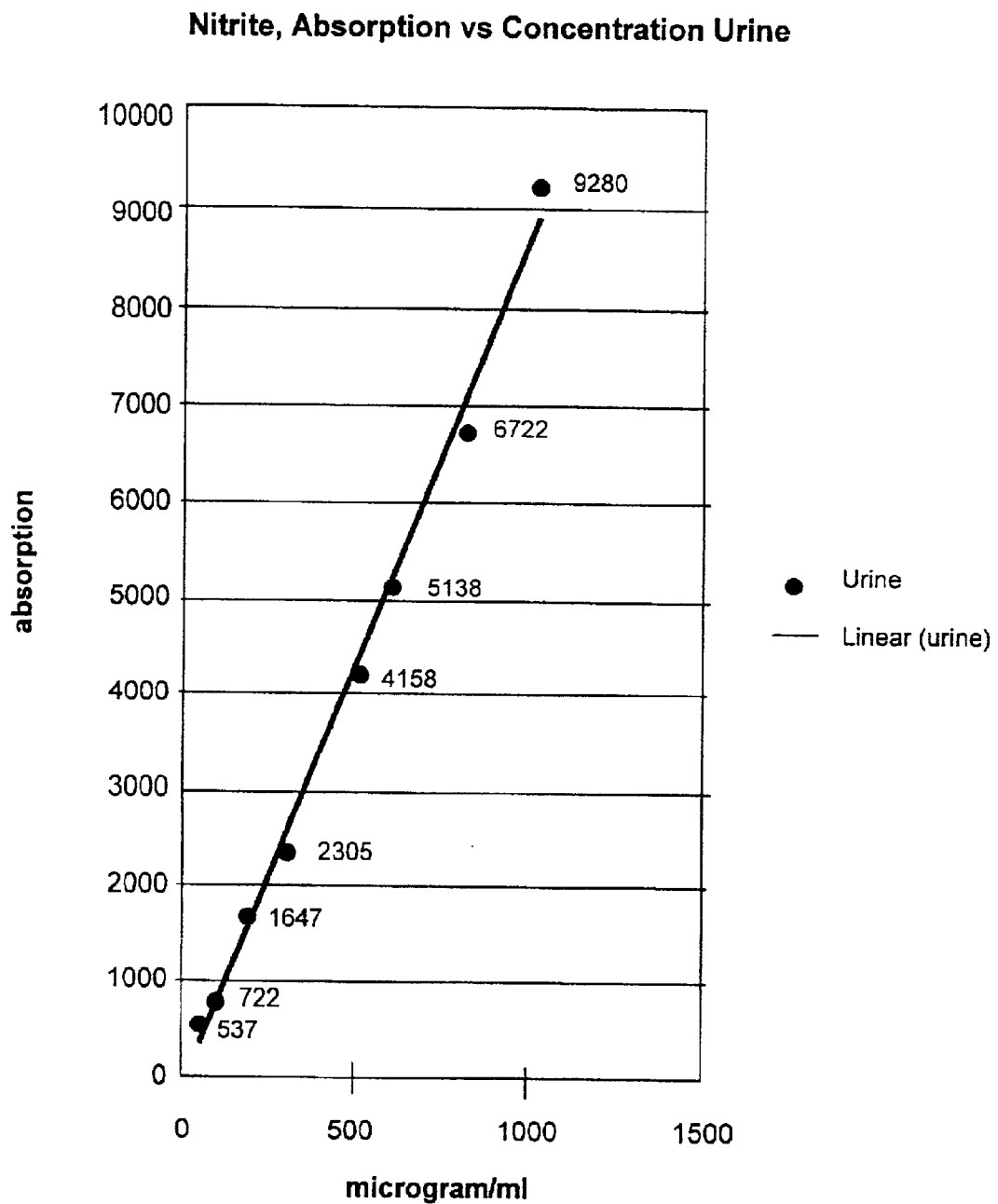
FIG. 4 is a graphical representation of measured concentration vs. spiked concentration data from an evaluation study involving solutions of sodium nitrite treated with DPD and creatinine.

Urine was spiked with various amounts of pyridinium chlorochromate as the starting point for generating an absorbance curve. Spiked samples were processed through an Olympus AU800 autoanalyzer which sampled a 3 µl aliquot of the spiked specimen, mixed it with 250 ml of the DPD/creatinine composition described in Example 1 and 250 ml of deionized water. The analyzer control software was set to S1=0 and E1=2 and a reading was taken at 540 nm. Table 4 contains the data from five runs and FIG. 4 is a graph of these results.

Based on the instrument printouts in concentration mode, readings less than −50 µg/ml are considered to reflect adulterated samples are subjected to alternative testing to confirm the presence or absence of pyridinium chlorochromate.

TABLE 4

Evaluation of Pyridinium Chlorochromate with DPD/creatinine Composition

| Conc. µg/ml | Assayed Values (concentration units) | | | | | Average |
|---|---|---|---|---|---|---|
| 50 | 40 | 41 | 42 | 36 | 42 | 40 |
| 75 | 60 | 61 | 63 | 62 | 63 | 62 |
| 112.5 | 85 | 89 | 92 | 86 | 87 | 88 |
| 125 | | 101 | 104 | 99 | 103 | 102 |
| 150 | 116 | 123 | 123 | 118 | 121 | 120 |
| 187.5 | 147 | 153 | 154 | 154 | 154 | 152 |
| 225 | 176 | 186 | | 175 | 172 | 177 |
| 500 | 372 | 403 | 403 | 407 | 390 | 395 |
| 1000 | 757 | 802 | 786 | 779 | 750 | 775 |
| 2000 | 1399 | 1472 | 1460 | 1410 | 1416 | 1431 |
| 3000 | 2017 | 2092 | 2110 | 2068 | 2045 | 2066 |
| 4000 | 2596 | 2724 | 2687 | 2665 | 2644 | 2663 |
| | Series 1 | Series 2 | Series 3 | Series 4 | Series 5 | Series 6 |

EXAMPLE 7(c)

Evaluation of DPD/Creatinine as a Test for Na Hypochlorite

Figure 5:
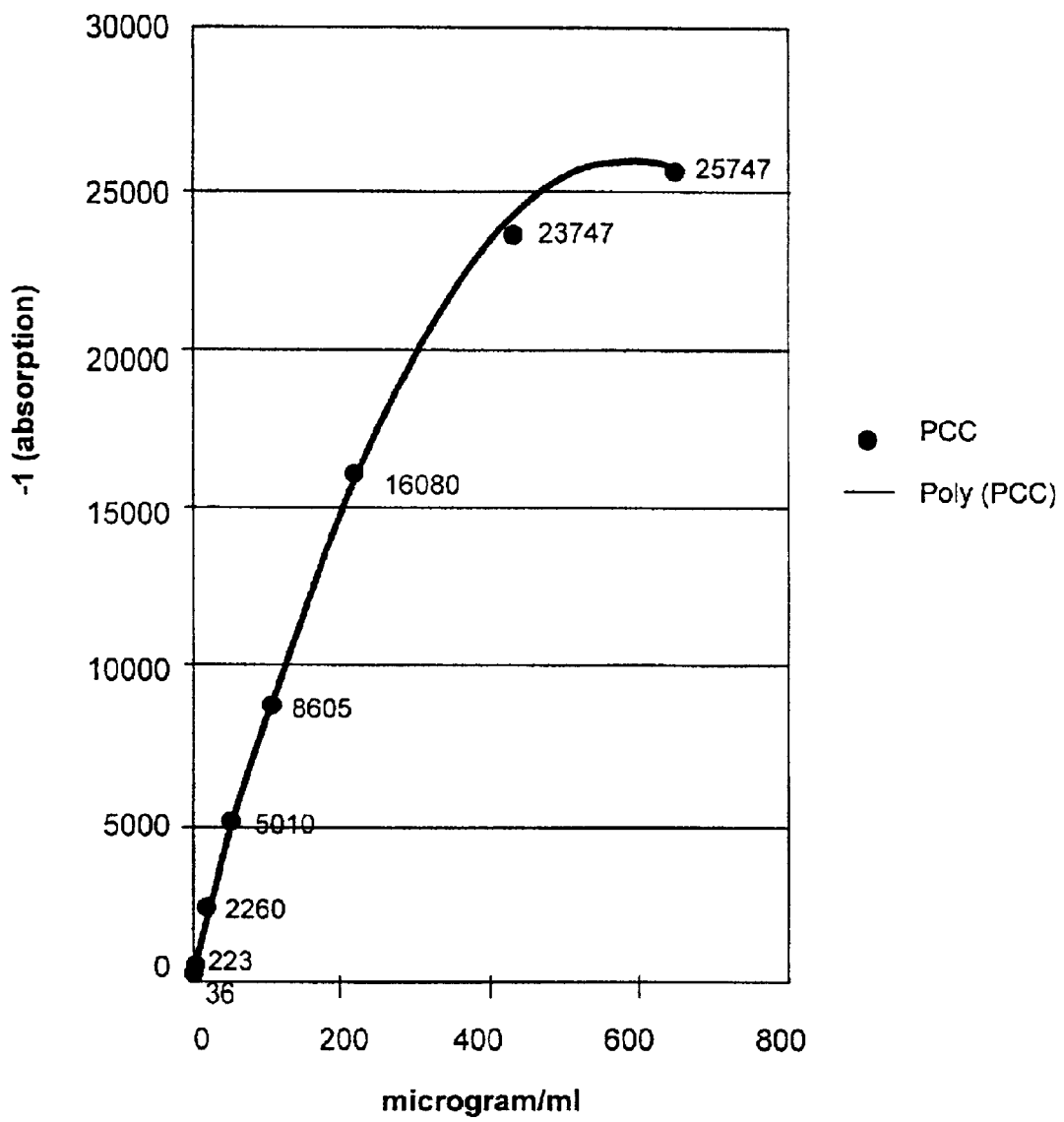
FIG. 5 is a graphical representation of measured concentration vs. spiked concentration data from an evaluation study involving solutions of pyridinium chlorochromate treated with DPD and creatinine.
Figure 6:
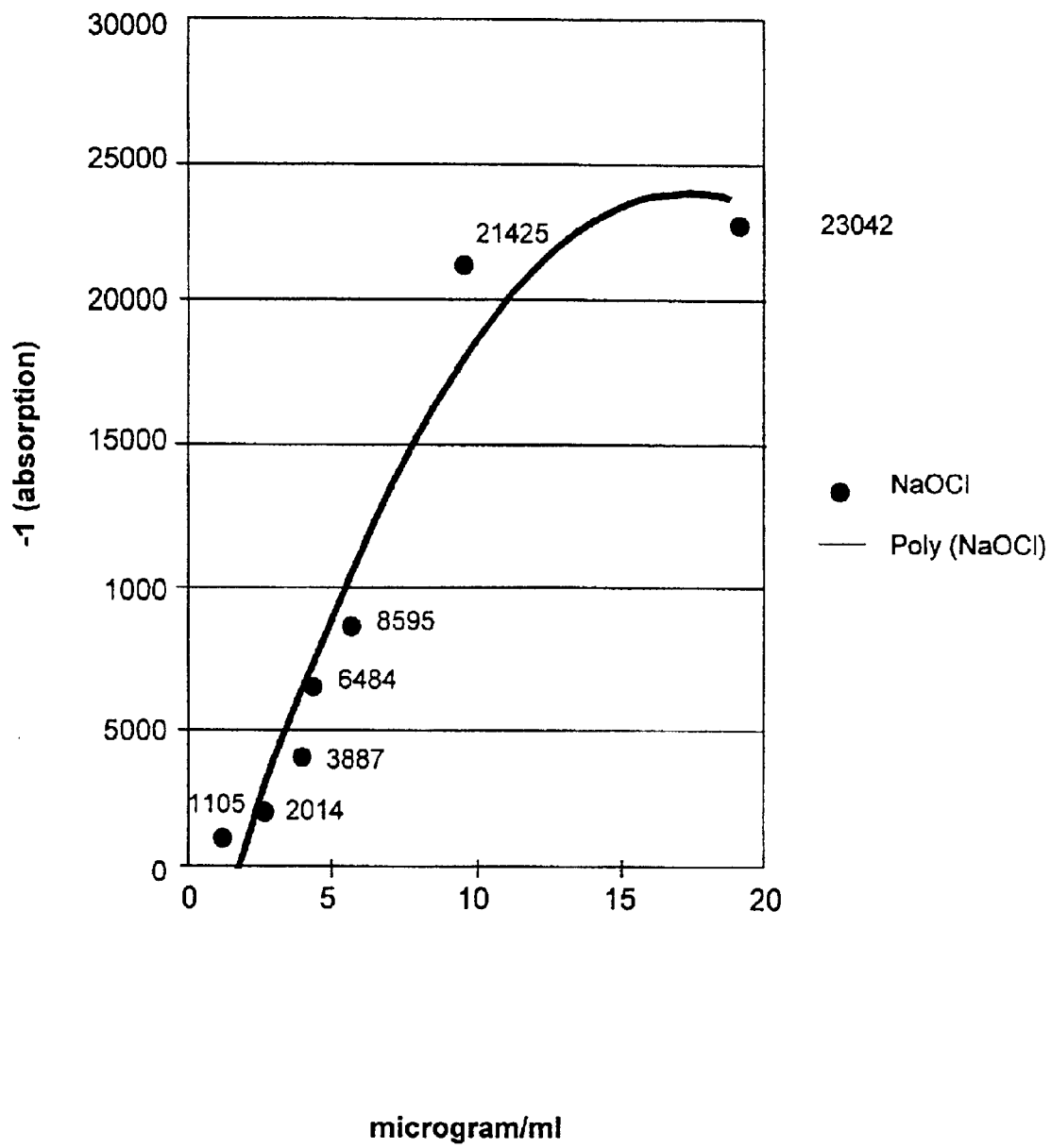
FIG. 6 is a graphical representation of measured concentration vs. spiked concentration data from an evaluation study involving solutions of sodium hypochlorite treated with DPD and creatinine.

Urine was spiked with various amounts of commercial bleach comprising about 5.25% of sodium hypochlorite as the starting point for generating an absorbance curve. Spiked samples were processed through an Olympus AU800 autoanalyzer which sampled a 3 µl aliquot of the spiked specimen, mixed it with 250 ml of the DPD/creatinine composition described in Example 1 and 250 ml of deionized water. The analyzer control software was set to S1=0 and E1=2 and a reading was taken at 540 nm, 30 seconds after mixing. Results are given in Table 5 and in graphic form in FIG. 5.

Based on the instrument printout in concentration mode, readings of greater than −50 μg/ml are considered to represent normal unadulterated samples and readings equal or less than −50 μg/ml or higher are confirmed by a second test for chlorine.

TABLE 5

Evaluation of Sodium Hypochlorite with DPD/Creatinine Composition

| Conc. μg/ml | Assayed Values (Absorbance units) | | | | | | Average |
|---|---|---|---|---|---|---|---|
| 0.03 | 61 | 9 | 36 | 42 | 9 | | 37 |
| 0.05 | 101 | 25 | 71 | 124 | 29 | | 80 |
| 0.13 | 256 | 158 | 231 | 183 | 103 | | 184 |
| 0.20 | 122 | | 303 | 234 | 147 | | 202 |
| 0.26 | 304 | 151 | 289 | 211 | 135 | | 218 |
| 0.33 | 267 | 143 | 275 | 191 | 131 | | 201 |
| 0.38 | 256 | 130 | 268 | 173 | 113 | | 188 |
| 0.53 | 278 | 269 | 747 | 390 | 349 | | 407 |
| 1.05 | 1734 | Abs Error | Abs Error | Abs Error | Abs Error | | |
| 1.58 | Abs Error | Abs Error | Abs Error | Abs Error | Abs Error | | |
| | Series 1 | Series 2 | Series 3 | Series 4 | Series 5 | Series 6 | |

While this invention has been described with respect to various specific examples and embodiments, it is to be understood that the invention is not limited thereto and that it can be variously practiced with the scope of the following claims.

What is claimed is:

1. A method for detecting the presence of at least one oxidizing agent in a urine sample, the method comprises the steps of:
   combining a composition with the urine sample to form a mixture, the composition comprises a primary aromatic amine and at least one stabilizer comprising a creatinine; and
   detecting from the mixture an absorbance band associated with the oxidizing agent.

2. A method of claim 1 wherein the oxidizing agent is selected from the group consisting of chelating complex, transition metals, chromium compounds (including chromate salts, pyridinium chlorochromate, pyridinium fluorochromate, chromium oxide, dichromate); nitrites (including sodium nitrite, alkyl nitrite, arylnitrite and a nitrous acid); nitrogen heterocyclic salts of oxidizing agents (including pyridinium hydrogen perbromide and quinolinum dichromate); peroxides (including hydrogen peroxide), hypohalites (including hypochlorite and hypobromite); ferricyanide; halites (including chlorite), halates (including chlorate), perhalate (including perchlorate), periodide, oxone, permanganate, N-chlorosulfonamides (including chloroamine-T, chloroamine-B), peracids (including perselenic acid, 3-chloroperbenzoic acid), oxidative enzymes (including catalase, peroxidase, microperoxidase), the like and mixtures thereof.

3. A composition of claim 1 wherein the presence of an oxidizing agent is identified by a presence of a broad band at about 470 nm to about 604 nm.

4. A method of claim 3 wherein the oxidizing agent is selected from the group consisting of chromium compounds, nitrogen heterocyclic salts of oxidizing agents and hypohalites.

5. A composition of claim 1 wherein the presence of the oxidizing agent is identified by a presence of a band at about 408 nm to about 420 nm.

6. A composition of claim 5 wherein the oxidizing agent is a nitrite.

7. A method of claim 1 wherein the primary aromatic amine comprises N,N-diethylphenylene diamine.

8. A method of claim 1 wherein the stabilizer comprises a citrate.

9. A method of claim 1 wherein the composition further comprises an iodide.

10. A method of claim 9, wherein the composition further comprises a citrate, and wherein the primary aromatic amine comprises a N,N-diethylenephenylene diamine.

11. A method for detecting the presence of at least an oxidizing agent in an aqueous sample, the method comprises the steps of:
    combining a composition with the aqueous sample to form a mixture, the composition comprises an N,N-diethylphenylene diamine and a creatinine; and
    detecting from the mixture an absorbance band associated with the oxidizing agent.

12. A method for detecting the presence of at least one oxidizing agent in an aqueous sample, the method comprises the steps of:
    combining a composition with the aqueous sample to form a mixture, the composition comprises an amine, an iodide and at least one stabilizer comprising a creatinine; and
    detecting from the mixture an absorbance band associated with the at least one oxidizing agent.

13. A method of claim 12 wherein the oxidizing agent is selected from the group consisting of chelating complex, transition metals, chromium compounds (including chromate salts, pyridinium chlorochromate, pyridinium fluorochromate, chromium oxide, dichromate); nitrites (including sodium nitrite, alkyl nitrite, arylnitrite and a nitrous acid); nitrogen heterocyclic salts of oxidizing agents (including pyridinium hydrogen perbromide and quinolinum dichromate); peroxides (including hydrogen peroxide), hypohalites (including hypochlorite and hypobromite); ferricyanide; halites (including chlorite), halates (including chlorate), perhalate (including perchlorate), periodide, oxone, permanganate, N-chlorosulfonamides (including chloroamine-T, chloroamine-B), peracids (including perselenic acid, 3-chloroperbenzoic acid), oxidative enzymes (including catalase, peroxidase, microperoxidase), the like and mixtures thereof.

14. A method of claims 12 wherein the aqueous sample comprises a body fluid, including urine.

15. A method of claim 12 wherein the amine comprises a primary aryl diamine.

16. A method of claim 12 wherein the amine comprises N,N-diethylphenylene diamine.

17. A method of claim 12 wherein the stabilizer comprises a citrate.

18. A composition of claim 12 wherein the presence of an oxidizing agent is identified by a presence of a broad band at about 470 nm to about 604 nm.

19. A composition of claim 18 wherein the oxidizing agent is selected from the group consisting of chromium compounds, nitrogen heterocyclic salts of oxidizing agents and hypohalites.

20. A method of claim 20 wherein the presence of the oxidizing agent is identified by a presence of a band at about 408 nm to about 420 nm.

21. A method of claim 20 wherein the oxidizing agent is a nitrite.

22. A method for detecting the presence of at least one adulterant in an aqueous sample, the method comprises the steps of:

adding the aqueous sample to a cuvette;

placing the cuvette into a spectrophotometer;

adding a composition to the sample in the cuvette by delivering the composition through an opening in the cuvette to form a mixture, the composition comprises an amine and at least one stabilizer comprising a creatinine; and detecting from the mixture an absorbance band associated with the adulterant.

23. A method for detecting at least one adulterant in a biological sample, comprising:

mixing a composition with a biological sample, the composition comprising N,N-diethyiphenylene diamine, creatinine, citric acid, and iodide, and detecting an absorption peak associated with the presence of the at least one adulterant.

24. The method of claim 23, wherein the biological sample is a urine sample.

25. The method of claim 23, wherein the at least one adulterant includes an oxidizing adulterant.

26. The method of claim 23, wherein the composition is mixed with the biological sample, and the composition forms a stabilized intermediate product that is stable for at least about two minutes.

27. The method of claim 23, wherein the method is automated.

28. The method of claim 23, wherein the at least one adulterant includes an oxidizing agent and a nitrite.

29. The method of claim 28, wherein the absorption peak associated with the nitrite has a wavelength between about 408 nm and about 410 nm.

30. The method of claim 28, wherein the absorption peak associated with the oxidizing agent has a wavelength between about 470 nm and about 620 nm.

* * * * *

UNITED STATES PATENT AND TRADEMARK OFFICE
CERTIFICATE OF CORRECTION

PATENT NO. : 6,861,262 B2
DATED : March 1, 2005
INVENTOR(S) : Novinski et al.

It is certified that error appears in the above-identified patent and that said Letters Patent is hereby corrected as shown below:

Column 15,
Lines 56, 63 and 65, after "A" change "composition" to -- method --.

Column 16,
Line 9, after "a" change "N,N-diethylenephenylene" to -- N,N-diethylphenylene --.
Line 60, after "claim" change "20" to -- 12 --.

Signed and Sealed this

Seventeenth Day of May, 2005

JON W. DUDAS
*Director of the United States Patent and Trademark Office*